United States Patent
Kim et al.

(10) Patent No.: US 9,464,945 B2
(45) Date of Patent: Oct. 11, 2016

(54) PROBE SENSOR CAPABLE OF MEASUREMENT FOR TEMPERATURE WITH STIMULUS

(71) Applicant: KOREA INSTITUTE OF SCIENCE AND TECHNOLOGY, Seoul (KR)

(72) Inventors: Jin Seok Kim, Seoul (KR); Jun-Kyo Francis Suh, Seoul (KR); Hyowon Moon, Gwacheon-si (KR)

(73) Assignee: Korea Institute of Science and Technology, Seoul (KR)

( * ) Notice: Subject to any disclaimer, the term of this patent is extended or adjusted under 35 U.S.C. 154(b) by 491 days.

(21) Appl. No.: 14/057,859

(22) Filed: Oct. 18, 2013

(65) Prior Publication Data

US 2014/0140372 A1    May 22, 2014

(30) Foreign Application Priority Data

Nov. 19, 2012    (KR) .......................... 10-2012-0130660

(51) Int. Cl.
*G01K 11/12* (2006.01)
*G01N 21/45* (2006.01)
*G01N 21/47* (2006.01)

(52) U.S. Cl.
CPC ............. *G01K 11/125* (2013.01); *G01N 21/45* (2013.01); *G01N 21/47* (2013.01)

(58) Field of Classification Search
CPC ........ G01K 11/125; G01K 5/48; G01K 5/00; G01N 25/00; G01N 21/47; G01N 21/45
USPC ................. 374/162, 161, 187, 191, 193, 194
See application file for complete search history.

(56) References Cited

U.S. PATENT DOCUMENTS

| 6,019,507 A * | 2/2000 | Takaki | G01K 11/18 374/161 |
| 6,141,098 A | 10/2000 | Sawatari et al. | |
| 2005/0259716 A1 * | 11/2005 | Ito | G01K 11/12 374/161 |
| 2009/0022453 A1 * | 1/2009 | Ueno | G02F 1/293 385/16 |
| 2009/0180516 A1 * | 7/2009 | Den Toonder | G01K 5/486 374/187 |
| 2009/0202194 A1 * | 8/2009 | Bosselmann | G01K 11/3206 385/12 |

(Continued)

FOREIGN PATENT DOCUMENTS

KR    10-2012-0043199      5/2012

OTHER PUBLICATIONS

Choi, Hae Young et al., "Miniature fiber-optic high temperature sensor based on a hybrid structured Fabry-Perot interferometer", Optical Society of America, Nov. 1, 2008, vol. 33, No. 21, pp. 2455-2457.

*Primary Examiner* — Lisa Caputo
*Assistant Examiner* — Philip Cotey
(74) *Attorney, Agent, or Firm* — NSIP Law

(57) ABSTRACT

A probe sensor has a probe structure having a probe body inserted into an experiment subject, a block body disposed on the probe body to transmit or reflect an incident light, and a light irradiation body for inputting a first incident light to the block body; a first light source for generating the first incident light and transmitting to the light irradiation body; and a light analyzer for analyzing a first reflection light which is a reflection light of the first incident light reflected by the block body, wherein the length of the block body changes according to a temperature change, and wherein the light analyzer measures a temperature change of the experiment subject by detecting a wavelength change of the first reflection light according to the length change of the block body.

10 Claims, 4 Drawing Sheets

(56) References Cited

U.S. PATENT DOCUMENTS

| | | | |
|---|---|---|---|
| 2009/0228234 A1* | 9/2009 | Abe | G01K 11/00 702/134 |
| 2010/0111136 A1* | 5/2010 | Huang | G01D 5/35303 374/161 |
| 2011/0044371 A1* | 2/2011 | Lee | G01M 11/319 374/161 |
| 2011/0312107 A1* | 12/2011 | Yves | C23C 14/541 438/14 |
| 2012/0059255 A1* | 3/2012 | Paul | A61N 1/327 600/431 |
| 2012/0062870 A1* | 3/2012 | Yamawaku | G01K 11/125 356/51 |
| 2012/0120984 A1* | 5/2012 | Vanier | B82Y 40/00 374/161 |
| 2012/0183015 A1* | 7/2012 | Hill | G01K 11/32 374/161 |
| 2012/0250724 A1* | 10/2012 | Ikeda | G01K 17/00 374/29 |

* cited by examiner

PROBE SENSOR CAPABLE OF MEASUREMENT FOR TEMPERATURE WITH STIMULUS

CROSS-REFERENCE TO RELATED APPLICATION

This application claims priority to Korean Patent Application No. 10-2012-0130660, filed on Nov. 19, 2012, and all the benefits accruing therefrom under 35 U.S.C. §119, the contents of which in its entirety are herein incorporated by reference.

BACKGROUND

1. Field

The present disclosure relates to a probe sensor directly inserted into an experiment subject to collect reaction information of the experiment subject, and more particularly, to a probe sensor capable of measurement for a temperature change at an insertion portion of the probe.

2. Description of the Related Art

Recently, a study for stimulating nerves or cells of an experiment subject and sensing and analyzing resultant signals to cure diseases and investigate reaction characteristics of living bodies is being actively researched.

In order to directly stimulate stimulating nerves or cells of an experiment subject and collect its information, a probe sensor capable of being inserted into the experiment subject is used.

In existing general probe sensors, the cerebral nerve is electrically stimulated using electrodes integrated at a probe body. If an electric stimulation is applied to nerves as described above, the experimented portion may be damaged. In addition, since nerves or cells are composed of electrically conductive substances, it is impossible to apply a local stimulation to a desired spot.

Therefore, a method for applying a light stimulation using light and collecting its reaction signal has been recently introduced.

However, if excessive heat is applied to nerves or cells of the experiment subject while applying a light stimulation, the tissues may come to necrosis.

In addition, a medicine may be injected for therapy or experiments into a portion in which the probe structure is inserted, but the injection of medicine may cause a temperature change at tissues.

Due to the above reasons, a local temperature change at the portion in which the probe structure is inserted should be monitored. However, an existing probe sensor is not able to measure a local temperature change at the insertion portion.

SUMMARY

The present disclosure is directed to providing a probe sensor capable of monitoring a temperature change at a local portion in which a probe is inserted.

In one aspect, there is provided a probe sensor, which includes: a probe structure having a probe body inserted into an experiment subject, a block body disposed on the probe body to transmit or reflect an incident light, and a light irradiation body for inputting a first incident light to the block body; a first light source for generating the first incident light and transmitting to the light irradiation body; and a light analyzer for analyzing a first reflection light which is a reflection light of the first incident light reflected by the block body, wherein the length of the block body changes according to a temperature change, and wherein the light analyzer measures a temperature change of the experiment subject by detecting a wavelength change of the first reflection light according to the length change of the block body.

In addition, the block body may include a first boundary surface and a second boundary surface perpendicular to the first incident light, and the light analyzer may measure a temperature change of the experiment subject by detecting a wavelength change of the first reflection light according to a length change between the first boundary surface and the second boundary surface, caused by the temperature change.

Moreover, the probe sensor may further include: a second light source for generating a second incident light which gives a light stimulation to the experiment subject and putting the second incident light to the light irradiation body; an electrode formed at the probe body to collect a reaction signal of the experiment subject generated by the second incident light; and a light distributer for separating the first reflection light from the reflection light reflected by the block body and sending the first reflection light to the light analyzer, wherein the second incident light may be a light having a wavelength band not overlapping with the first incident light.

In addition, the light irradiation body may be an optical fiber disposed on the probe body along the length direction of the probe body.

Moreover, the block body may be formed near a tip of the probe body.

In addition, the block body may be formed with a polymer made of transparent material.

Moreover, a channel for injecting a medicine to the experiment subject may be formed at the probe body.

BRIEF DESCRIPTION OF THE DRAWINGS

The above and other aspects, features and advantages of the disclosed exemplary embodiments will be more apparent from the following detailed description taken in conjunction with the accompanying drawings in which.

DETAILED DESCRIPTION

Figure 1:
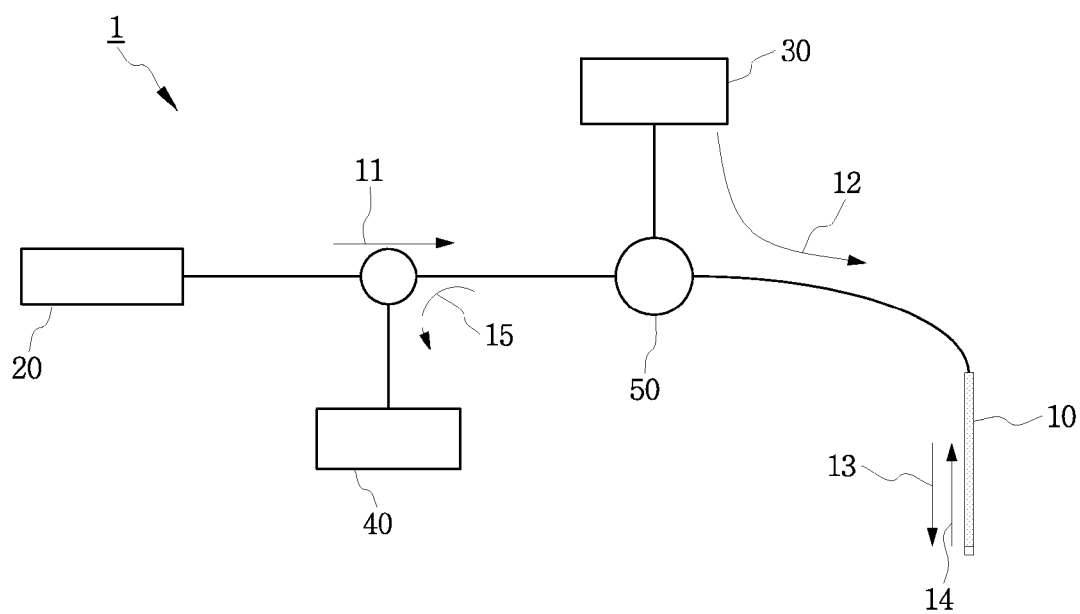
FIG. 1 is a diagram showing a probe sensor according to an embodiment of the present disclosure.

Hereinafter, an embodiment of the present disclosure will be described with reference to the accompanying drawings. Even though the present disclosure is described with reference to the embodiment depicted in the drawings, this is just an example, and the spirit, essence and operations of the present disclosure are not limited thereto.

FIG. 1 is a diagram showing a probe sensor 1 according to an embodiment of the present disclosure.

As shown in FIG. 1, the probe sensor 1 includes a probe structure 10 for transmitting a stimulation to an experiment subject and collecting a reaction, a first light source 20 for generating a first incident light 11 used for measuring a temperature, a second light source 30 for generating a second incident light 12 used for a light stimulation with respect to the experiment subject, a light analyzer 40 for analyzing an incident light signal, and a light distributer 50 for separating a first reflection light 15 corresponding to a reflection light of the first incident light 11 from the reflection light 14 reflected by the probe structure 10 and sending the first reflection light 15 to a light analyzer 40.

Figure 2:
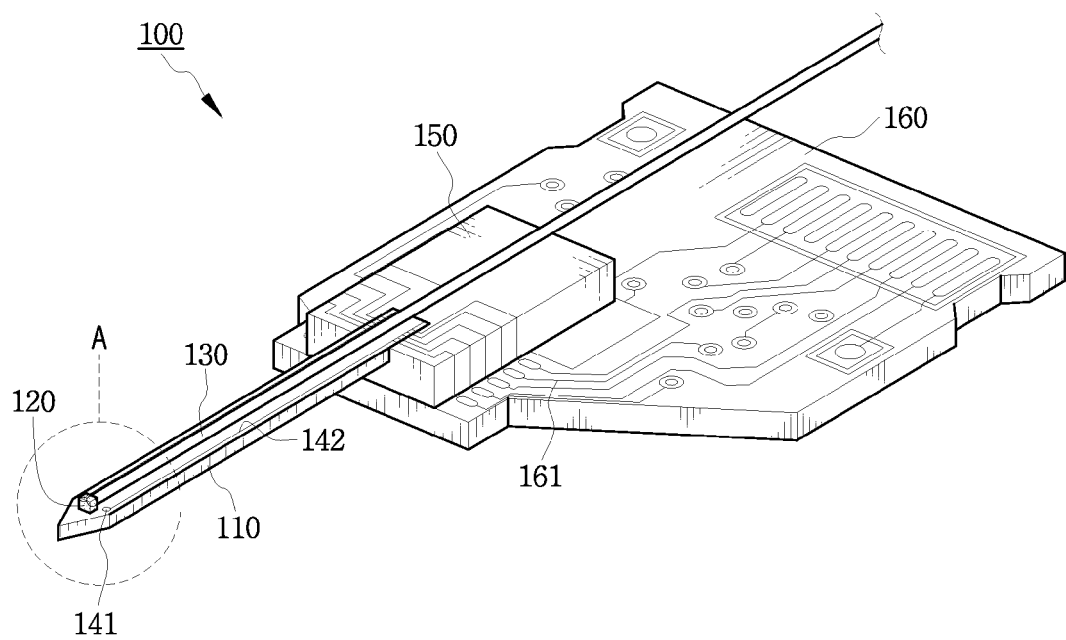
FIG. 2 is a perspective view showing a probe structure according to an embodiment of the present disclosure.
Figure 3:
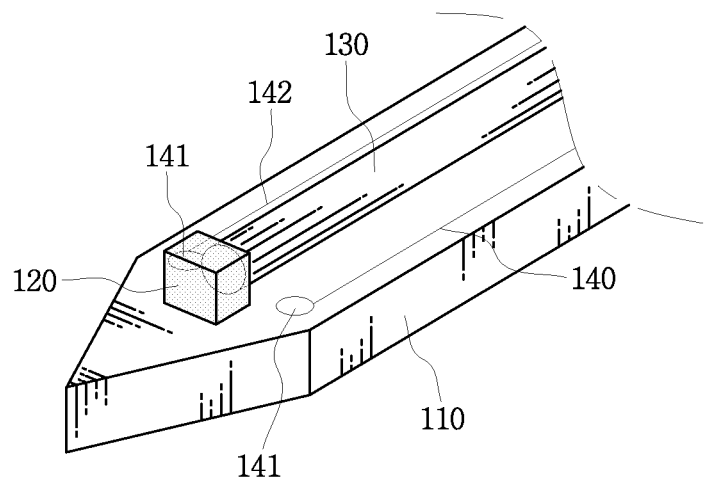
FIG. 3 is an enlarged perspective view showing the portion A of FIG. 2.
Figure 4:
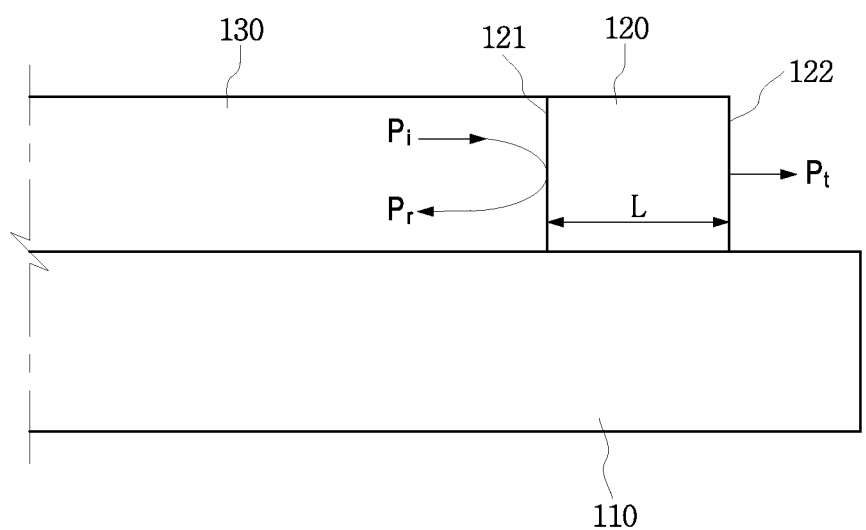
FIG. 4 is an enlarged side view showing the portion A.

FIG. 2 is a perspective view showing a probe structure 100 according to an embodiment of the present disclosure, FIG. 3 is an enlarged perspective view showing the portion A of FIG. 2, and FIG. 4 is an enlarged side view showing the portion A.

As shown in FIGS. 2 to 4, the probe structure 100 of this embodiment includes a probe body 110 extending by a predetermined length to be inserted into the experiment subject and having a sharp tip, a fixing body 150 for fixing the probe body 110, and a substrate 160 to which the fixing body 150 is attached.

A block body 120 made of transparent material to transmit or reflect an incident light is formed near the tip on the probe body 110, and a light irradiation body 130 extending along the length direction of the probe body 110 is disposed at the upstream of the block body 120 to irradiate a light toward the block body 120. According to this embodiment, an optical fiber is used as the light irradiation body 130. The term "upstream" used herein means a side from which a light advances, and the term "downstream" means a side to which a light progresses.

An electrode array 141 for collecting a reaction signal from the experiment subject is integrated at both sides of the upstream end of the light irradiation body 130, and an electric wire 142 electrically connected to the electrode array 141 extends to the fixing body 150 along the length direction of the probe body 110 and is electrically connected to a wiring 161 which is electrically connected to the substrate 160.

The block body 120 has a rectangular parallelepiped shape and is made of transparent SU-8 polymer material.

As well shown in FIG. 4, the block body 120 has a first boundary surface 121 and a second boundary surface 122 formed in parallel to each other. The first boundary surface 121 and the second boundary surface 122 are formed perpendicular to a path of light incident by the light irradiation body 110. An end surface at the downstream of the light irradiation body 130 from which a light is output is closely adhered to the first boundary surface 121. Therefore, the light irradiated from the light irradiation body 130 is reflected by two boundary surfaces (the first boundary surface 121 and the second boundary surface 122).

The block body 120 of this embodiment may change its length according to a temperature change, and if a temperature changes, a distance L between the first boundary surface 121 and the second boundary surface 122 increases or decreases with a thermal expansion coefficient of 52 ppm.

If the probe sensor 1 of this embodiment is used, it is possible to apply a light stimulation to nerves or cells of the experiment subject and also monitor a temperature change of the nerves or cells caused by the light stimulation.

Referring to FIG. 1 again, the first light source 20 generates the first incident light 11, which is an infrared ray having a wavelength band of 1530 nm (about 1500 nm to 1560 nm), and inputs the first incident light to the light irradiation body 130 of the probe structure. Simultaneously, the second light source 30 generates the second incident light 12, which is a blue ray having a wavelength band of 470 nm (about 430 nm to 490 nm), and inputs the second incident light to the light irradiation body 130.

The frequency bands of 1530 nm and 470 nm are just examples, and it should be understood that lights of other wavelength bands not overlapping with each other may also be used as the first incident light 11 and the second incident light 12.

In addition, the second incident light 12 is not limited to a blue light. For example, the second incident light 12 may also be a light having a certain wavelength band using an opto-genetic principle in which a cell containing an aberrant gene reacts with different lights depending on a modifying substance when a light stimulation is applied thereto, or an infrared light which may give a stimulation by simply raising temperature of cells without any aberrant gene.

Moreover, the first incident light 11 is not limited to an infrared light, and any light not overlapping with the second incident light 12 may be applied as the first incident light 11 of this embodiment.

The mixed incident light 13 of the first incident light 11 and the second incident light 12 input to the light irradiation body 130 is irradiated to the block body 120.

Since the block body 120 is made of transparent material, almost the whole incident light 13 passes through the block body 120, but a part of the incident light 13 is reflected to progress toward the light source through the light irradiation body 130.

The mixed reflection light 14 is incident to the light distributer 50, and the light distributer 50 separates only a light of a wavelength band of 1530 nm (the first reflection light 15) corresponding to a reflection light of the first incident light 11 from the mixed reflection light 14 and sends it to the light analyzer 40 in order to analyze temperature.

Among the mixed incident light 13 passing through the block body 120, the second incident light 12 is a blue light with a high energy density and gives a light stimulation to cells or nerves of the experiment subject.

The stimulated portion reacting with the applied light stimulation generates a reaction signal, and the reaction signal is collected by the electrode array 141 integrated at the probe body 110. The reaction signal information collected by the electrode array 141 is transmitted through the electric wire 142 and the wiring 161 to the substrate 160 and received at an external computer (not shown). The received reaction signal information is used for analyzing a light reacting characteristic of the experiment subject.

Meanwhile, among the reflection light reflected by the block body 120, the first reflection light 15 is used for sensing a temperature change of the portion stimulated by the light stimulation.

Hereinafter, a principle for measuring a temperature change will be described with reference to FIG. 4.

In case of the block body 120 which is a transparent body having two boundary surfaces 121, 122 spaced apart by a distance L, if an incident light Pi is incident perpendicular to the boundary surfaces 121, 122, a reflection light reflected by each boundary surface is output. At this time, due to a difference in paths between the reflection light reflected by the first boundary surface 121 and the reflection light reflected by the second boundary surface 122, a finally output reflection light Pr has a specific wavelength spectrum.

Figure 5:
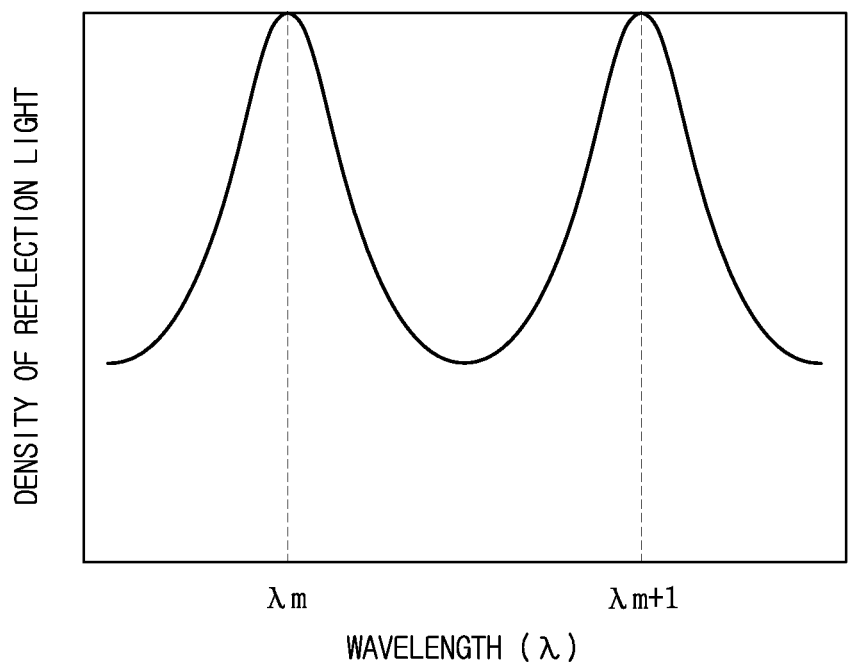
FIG. 5 shows a part of a wavelength spectrum of reflection lights reflected by two boundary surfaces.

FIG. 5 shows a part of a wavelength spectrum of the reflection light Pr.

As shown in FIG. 5, if an incident light Pi having a great wavelength band is input to an article having two boundary surfaces, due to the interference between two boundary surfaces, the reflection light Pr generates a wavelength spectrum having peaks at specific wavelength $\lambda_m$, $\lambda_{m+1}$, . . . .

At this time, if the intensity of the transmitted light Pt passing through the transparent article is much greater than the intensity of the reflection light Pr, the wavelength $\lambda_m$ may be expressed like Equation 1 below, as well known in the art.

$$\lambda_m = \frac{nL}{m} \quad \text{Equation 1}$$

where, n is a reflection of the block body 120.

In other words, it may be understood that the wavelength representing each peak is proportional to the length of the block body 120 (the distance L between the first boundary surface and the second boundary surface).

Figure 6:
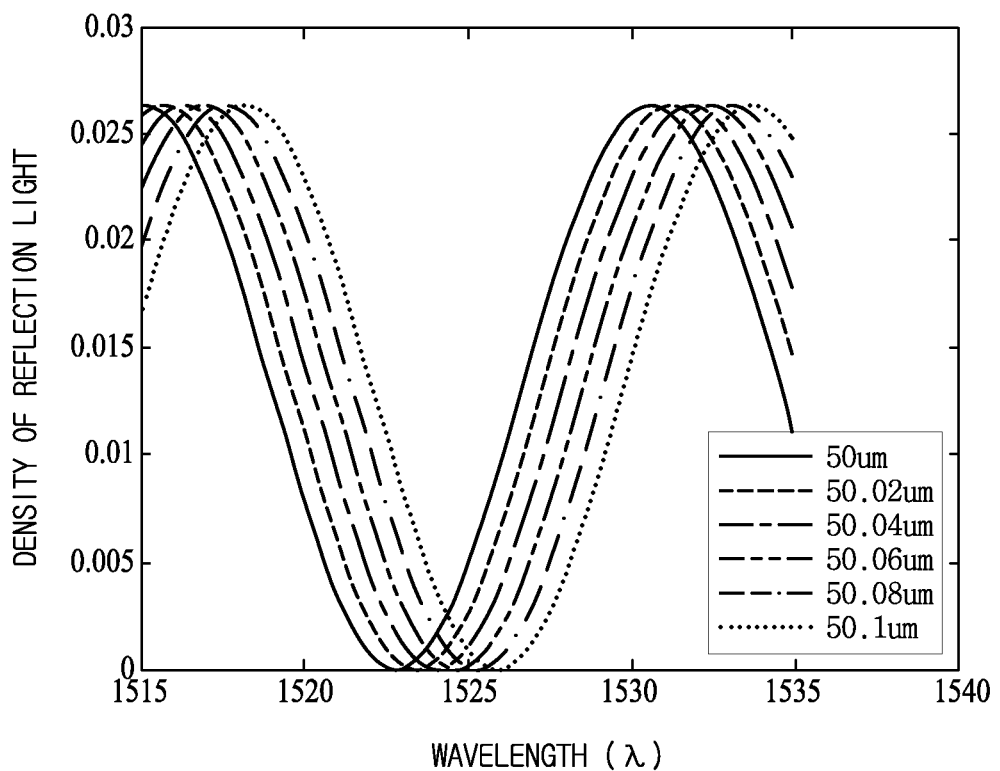
FIG. 6 shows a wavelength spectrum of a reflection light reflected by a block body when the length of the block body extends.

FIG. 6 shows a wavelength spectrum of the first reflection light 15 reflected by the block body 120 when the length of the block body 120 extends.

FIG. 6 shows a wavelength spectrum when the block body 120 having an initial length L of 50 μm extends by 0.02 μm. As shown in FIG. 6, it may be found that each peak of a wavelength curve moves to the right at regular intervals.

As described above, since the wavelength change amount $\lambda_m'$ representing a peak as the length L of the block body 120 changes into a length L' may be figured out, the length change amount $\Delta L$ of the block body 120 may be calculated as in Equation 2 below by using Equation 1.

$$\Delta L = L' - L = \frac{m}{n}(\lambda_m' - \lambda_m) \quad \text{Equation 2}$$

If the obtained length change amount $\Delta L$ is calculated with a thermal expansion coefficient, a temperature change at a portion where the block body 120 is located may be figured out.

As described above, if the probe sensor 1 of this embodiment is used, it is possible to sense a temperature change of a portion to which a light stimulation is applied, which prevents necrosis of tissues at the stimulated portion in advance.

Figure 7:
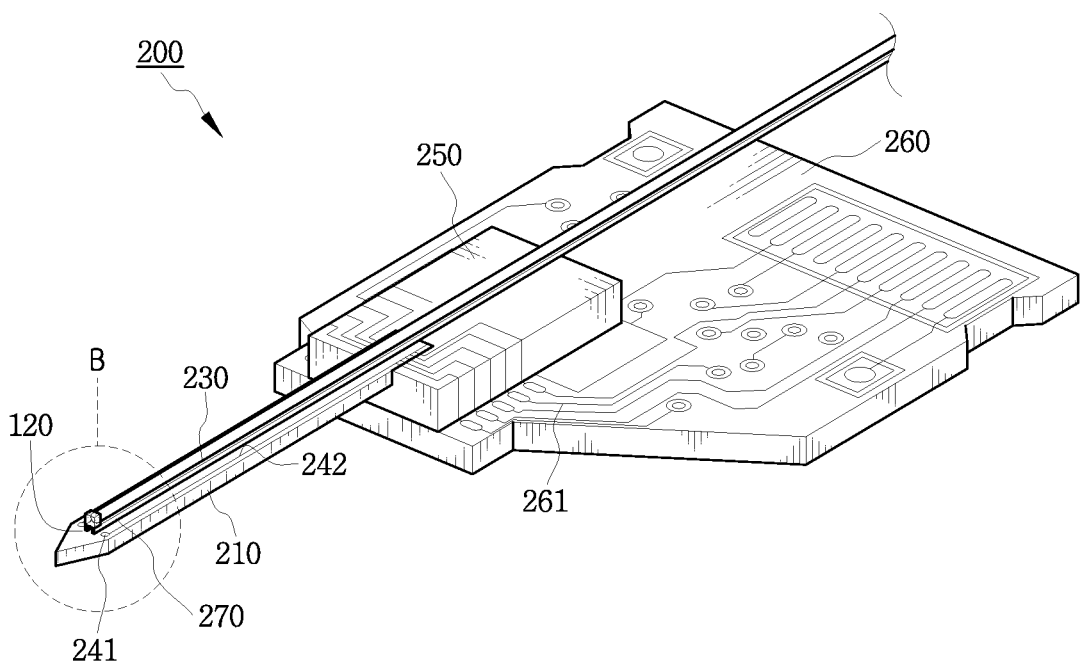
FIG. 7 is a perspective view showing a probe structure according to another embodiment of the present disclosure.
Figure 8:
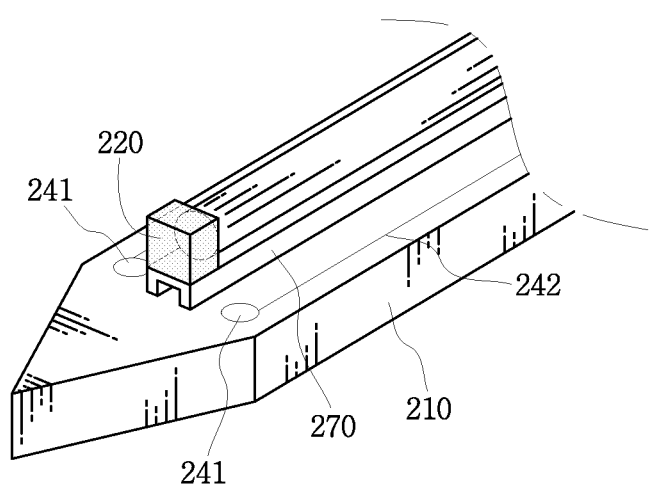
FIG. 8 is an enlarged view showing the portion B of FIG. 7.

FIG. 7 is a perspective view showing a probe structure 200 according to another embodiment of the present disclosure, and FIG. 8 is an enlarged view showing the portion B of FIG. 7.

In this embodiment, a channel 270 having a "⊂" shape capable of injecting a medicine is formed at a probe body 210 along the length direction thereof.

A light irradiation body 230 made of an optical fiber and a block body 220 are formed on a channel 270. At this time, the block body 220 is closely adhered to an end surface at the downstream of the light irradiation body 230.

Configuration of the probe structure 200 other than the channel 270 is substantially identical to that of the probe structure 100 according to the former embodiment and is not described in detail here.

Corresponding components of the probe structure 100 and the probe structure 200 are distinguished with hundred's digits, for example 100 and 200 and have the same ten's digit and unit's digit.

If the probe structure 200 is coupled to the probe sensor 1 instead of the probe structure 100 of the former embodiment, it is possible to inject a medicine into an experiment subject through the channel 270 in addition to applying a light stimulation to the experiment subject by using an optical fiber. A temperature change of the experiment subject, caused by such a light stimulation and/or the medicine injection, may be monitored by sensing a wavelength change of the reflection light according to a length change of the block body 120, in the same principle as described above.

What is claimed is:

1. A probe sensor, comprising:
    a probe structure including:
        a probe body configured to be inserted into an experiment subject,
        a block body disposed on a top surface of the probe body, configured to transmit or reflect an incident light, and having a length configured to change in response to a temperature change, and
        a light irradiation body disposed on a top surface of the probe body, and configured to irradiate a first incident light to the block body;
    a first light source configured to generate the first incident light and transmit the first incident light to the light irradiation body; and
    a light analyzer configured to analyze a first reflection light, wherein the first reflection light comprises the first incident light reflected by the block body,
    wherein the light analyzer is configured to measure a temperature change of the experiment subject, by detecting a wavelength change of the first reflection light in response to a change of length of the block body.

2. The probe sensor according to claim 1,
    wherein the block body includes a first boundary surface and a second boundary surface disposed perpendicular to the first incident light, and
    wherein the light analyzer is configured to measure a temperature change of the experiment subject, by detecting a wavelength change of the first reflection light in response to a length change between the first boundary surface and the second boundary surface, caused by the temperature change.

3. The probe sensor according to claim 1, further comprising:
    a second light source configured to generate a second incident light, wherein the second incident light gives a light stimulation to the experiment subject and puts the second incident light to the light irradiation body;
    an electrode formed on or in the probe body, and configured to collect a reaction signal of the experiment subject, wherein the reaction signal is generated by the second incident light; and
    a light distributer configured to separate the first reflection light from reflection light reflected by the block body, and to send the first reflection light to the light analyzer,
    wherein the second incident light has a wavelength band that does not overlap with a wavelength band of the first incident light.

4. The probe sensor according to claim 3,
wherein the light irradiation body comprises an optical fiber disposed on the probe body and along the length direction of the probe body.

5. The probe sensor according to claim 1,
wherein the block body is formed near a tip of the probe body.

6. The probe sensor according to claim 1,
wherein the block body comprises a transparent polymer.

7. The probe sensor according to claim 1,
wherein a channel configured to inject a medicine to the experiment subject is formed in the probe body.

8. The probe sensor according to claim 1,
wherein the probe body has an elongated shape.

9. The probe sensor according to claim 1, further comprising:
a fixing body; and
a substrate attached to the fixing body.

10. The probe sensor according to claim 9, further comprising:
an electrode array disposed on a tip of the probe body;
a wiring which is electrically connected to the substrate; and
an electric wire disposed along the probe body in a length direction, from the tip of the probe body to the fixing body, and electrically connected to the electrode array and to the wiring.

* * * * *